(12) United States Patent
Hsu

(10) Patent No.: US 6,773,416 B1
(45) Date of Patent: Aug. 10, 2004

(54) SAFETY HYPODERMIC SYRINGE

(76) Inventor: Fu-Yu Hsu, No. 407, Kuo Chi Road, Sec. 2, Tayuan Hsiang, TaoYuan Hsien (TW)

( * ) Notice: Subject to any disclaimer, the term of this patent is extended or adjusted under 35 U.S.C. 154(b) by 0 days.

(21) Appl. No.: 10/372,132

(22) Filed: Feb. 25, 2003

(51) Int. Cl.$^7$ .............................................. A61M 5/00
(52) U.S. Cl. ....................................... 604/110; 604/228
(58) Field of Search ................................ 604/110, 181, 604/187, 192, 195, 197, 228

(56) References Cited

U.S. PATENT DOCUMENTS 5,242,400 A * 9/1993 Blake et al. ................. 604/110
5,569,203 A * 10/1996 Chen ........................... 604/110

* cited by examiner

*Primary Examiner*—Kevin C. Sirmons
(74) *Attorney, Agent, or Firm*—Rosenberg, Klein & Lee

(57) ABSTRACT

A safety hypodermic syringe in which the plunger is detachably connected to the stopper by a hook joint so that when the user pulled the plunger backwards to carry the stopper and the needle assembly backwards to the inside of the barrel after the service of the syringe, the plunger is automatically disconnected from the stopper, leaving the stopper and the needle assembly inside the barrel.

7 Claims, 9 Drawing Sheets

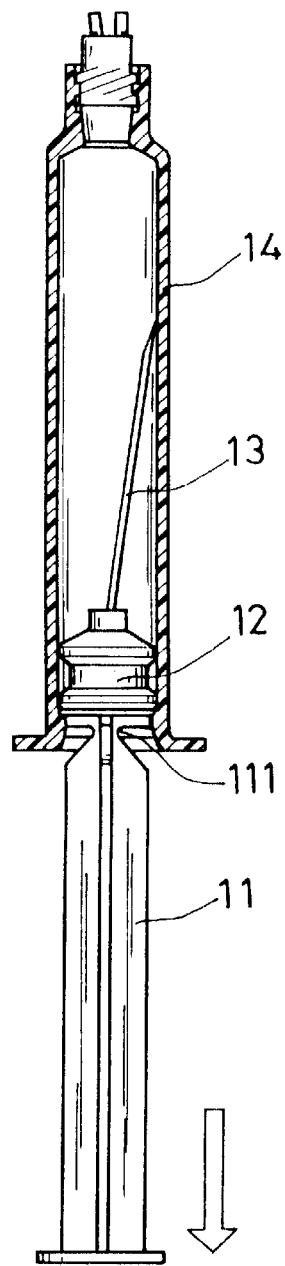
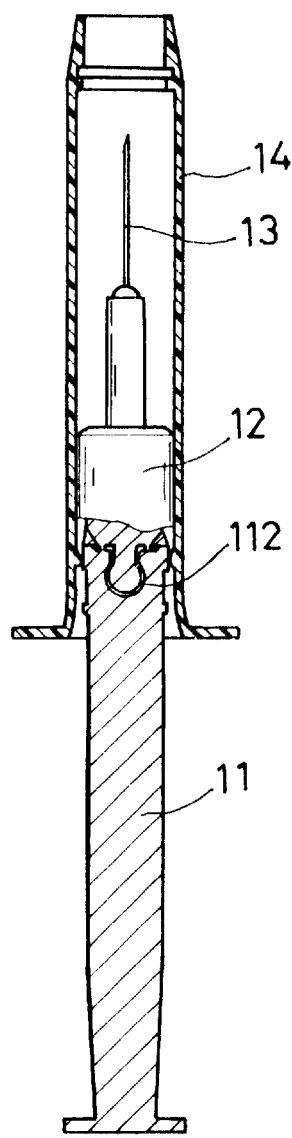
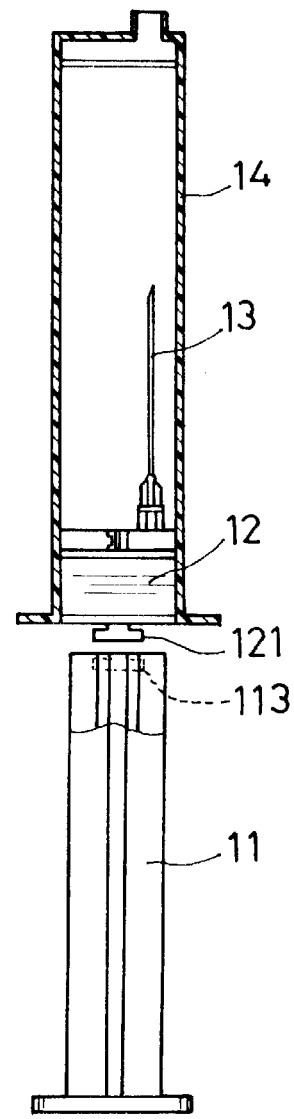
F I G. 1
PRIOR ART
F I G. 2
PRIOR ART
F I G. 3
PRIOR ART

SAFETY HYPODERMIC SYRINGE

BACKGROUND OF THE INVENTION

1. Field of the Invention

The present invention relates generally to a hypodermic syringe and, more particularly, to a safety hypodermic syringe, which enables the plunger to be automatically disconnected from the stopper after the service of the syringe, leaving the stopper and the needle assembly inside the barrel.

2. Description of the Related Art

When disposing of a disposable hypodermic syringe after its service, the person handling the disposable hypodermic syringe may be injured by the protruding needle cannula accidentally. In order to eliminate this problem, safety hypodermic syringes are developed. These safety hypodermic syringes enable the needle assembly to be pulled backwards with the plunger and received inside the barrel after the service. Exemplars of these safety hypodermic syringes are seen in Taiwan Patent Application Nos. 189436; 356013; 463639; 414085; 384709; 359621; 492328; 467752; 475449; 480185; 497976; 430565; 471322; 332433; 394027; and 447310, and U.S. Pat. Nos. 5,385,557; 4,747,830; 4,677,980; 5,242,400; 4,986,813; 4,947,863; 5,533,975; 5,171,300; 4,944,723, . . . etc. These safety hypodermic syringes still have drawbacks. When the needle assembly received inside the barrel after the service of the hypodermic syringe, the plunger is still maintained secured to the stopper and the barrel. If the person disposing of the hypodermic syringe pushes the plunger accidentally, the needle cannula may be forced out of the barrel to injure the person disposing of the hypodermic syringe or a nearby person. In order to eliminate this problem, safety hypodermic syringes with a disconnectable plunger are developed. FIG. 1 shows a safety hypodermic syringe according to the prior art. According to this design, the plunger 11 has a neck 111 near the front side. When the needle assembly 13 and the stopper 12 received inside the barrel 14 upon a return stroke of the plunger 11, the user can twist the plunger 11 to break the neck 111. U.S. Pat. No. 4,944,723 shows a similar design. FIG. 2 shows a safety hypodermic syringe according to Taiwan Patent Publication NO. 492328. According to this design, a breaking groove 112 is provided in the connecting area between the plunger 11 and the stopper 12. When the needle assembly 13 and the stopper 12 received inside the barrel 14 upon a return stroke of the plunger 11, the user can disconnect the plunger 11 from the stopper 12 by biasing the plunger 11. U.S. Pat. No. 5,242,400 shows a similar design. FIG. 3 shows a safety hypodermic syringe according to Taiwan Patent Publication No. 378541. According to this design, the stopper 12 has a T-block 121 invertedly suspended at the bottom side, and the plunger 11 has a front coupling hole 113 detachably coupled to the T-block 121. When disconnecting the plunger 11 from the stopper 12, the user must twist the plunger 11 with force.

SUMMARY OF THE INVENTION

The present invention has been accomplished under the circumstances in view. It is the main object of the present invention to provide a safety hypodermic syringe, which enables the plunger to be automatically disconnected from the stopper after the service of the syringe, leaving the stopper and the needle assembly inside the barrel.

To achieve this and other object of the present invention, the safety hypodermic syringe comprises a barrel, the barrel comprising a body and a socket at a front side of the body; a needle assembly, the needle assembly comprising a needle hub mounted in the front socket of the barrel, the needle hub having a bottom retaining hole, and a needle cannula forwardly extended from the needle hub outside the barrel; and a plunger and stopper unit, the plunger and stopper unit comprising a stopper fitted into the body of the barrel, and an elongated plunger adapted to reciprocate the stopper in the body of the barrel, the stopper having an arrowhead-like front hook engageable into a bottom retaining hole of the needle hub for enabling the needle assembly to be pulled backwards with the plunger and stopper unit and received inside the body of the barrel; wherein the barrel has a stop device in a rear side of the body and adapted to stop the stopper from falling out of the body; the plunger comprises a plurality of equiangularly spaced and radially extended springy front wings, the front wings each having a crevice longitudinally extended to a front side thereof, the front wings including two opposite front wings, the opposite front wings each having a plurality of retaining blocks; the stopper has a plurality of locating blocks protruded from a bottom sidewall thereof and defining a receiving space adapted to receive the front wings of the plunger, the locating blocks each having a protruded engagement portion adapted to engage the retaining blocks of the opposite front wings of the plunger and to secure the plunger to said stopper. dr

BRIEF DESCRIPTION OF THE DRAWINGS

FIG. 1 is a sectional side view of a safety hypodermic syringe according to the prior art.

FIG. 2 is a sectional side view of another design of safety hypodermic syringe according to the prior art.

FIG. 3 is a sectional side view of still another design of safety hypodermic syringe according to the prior art.

DETAILED DESCRIPTION OF THE INVENTION

Figure 4:
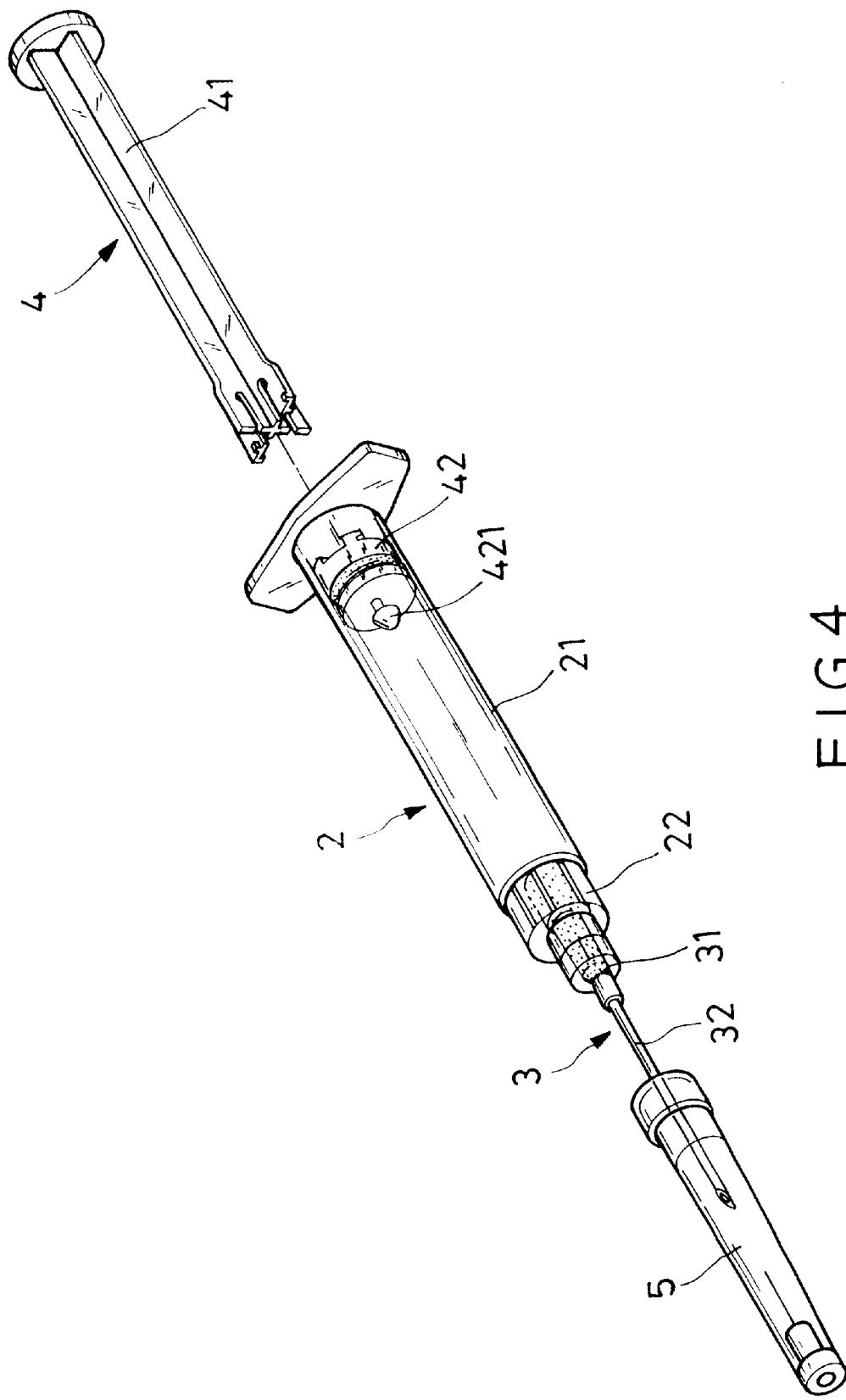
FIG. 4 is an exploded view of a safety hypodermic syringe according to the present invention.

Referring to FIG. 4, a safety hypodermic syringe in accordance with the present invention is shown comprised of a barrel 2, which comprises a body 21 and a socket 22 at the front side of the body 21, a needle assembly 3, which comprises a needle hub 31 mounted in the front socket 22 of the barrel 2 and a needle cannula 32 forwardly extended from the needle hub 31 outside the barrel 2, a plunger and stopper unit 4, which comprises a stopper 42 fitted into the body 21 of the barrel 2 and an elongated plunger 41 adapted to reciprocate the stopper 42 in the body 21 of the barrel 2, and a cap 5 adapted to protect the needle assembly 3. The stopper 42 has an arrowhead-like front hook 421 that can be hooked in a bottom retaining hole (not shown) in the needle hub 31 for enabling the needle assembly 3 to be pulled backwards with the plunger and stopper unit 4 and received inside the body 21 of the barrel 2.

Figure 5:
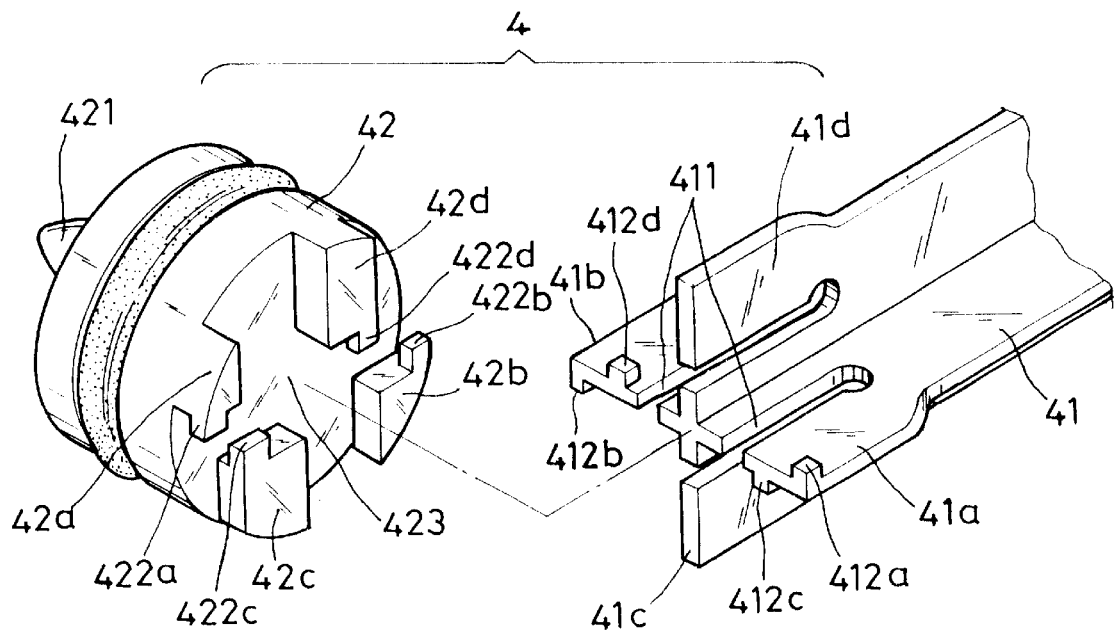
FIG. 5 is an exploded view of the plunger and stopper unit of the safety hypodermic syringe according to the present invention.

FIG. 5 is an exploded view of the aforesaid plunger and stopper unit 4. The plunger 41 comprises four equiangularly spaced and radially extended springy front wings 41a, 41b, 41c, and 41d, each having a crevice 411 longitudinally extended to the front side. The front wings 41a, 41b, 41c, and 41d are arranged in two pairs each including two opposite wings. Two opposite wings 41a and 41b each have two reversely protruded retaining blocks 412a and 412c; 412b and 412d. The stopper 42 has four locating blocks 42a, 42b, 42c, and 42d protruded from the bottom sidewall and defining a crossed receiving space 423 for receiving the front wings 41a, 41b, 41c, and 41d of the plunger 41. The locating blocks 42a, 42b, 42c, and 42d each have a protruded engagement portion 422a, 422b, 422c, or 422d adapted to engage the retaining blocks 412a and 412c, 412b, and 412d of the plunger 41.

Figure 6:
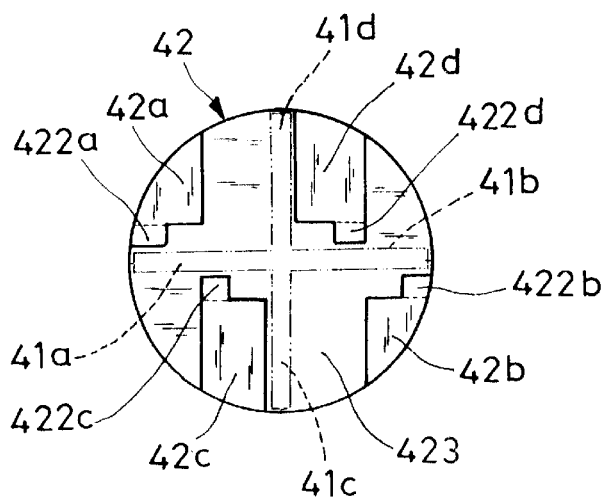
FIG. 6 is a bottom view of the stopper of the plunger and stopper unit of the safety hypodermic syringe according to the present invention.

FIG. 6 is a bottom view of the stopper 42 in which the imaginary lines indicate the positioning of the front wings 41a, 41b, 41c, and 41d of the plunger 41 relative to the locating blocks 42a, 42b, 42c, and 42d.

Figure 7:
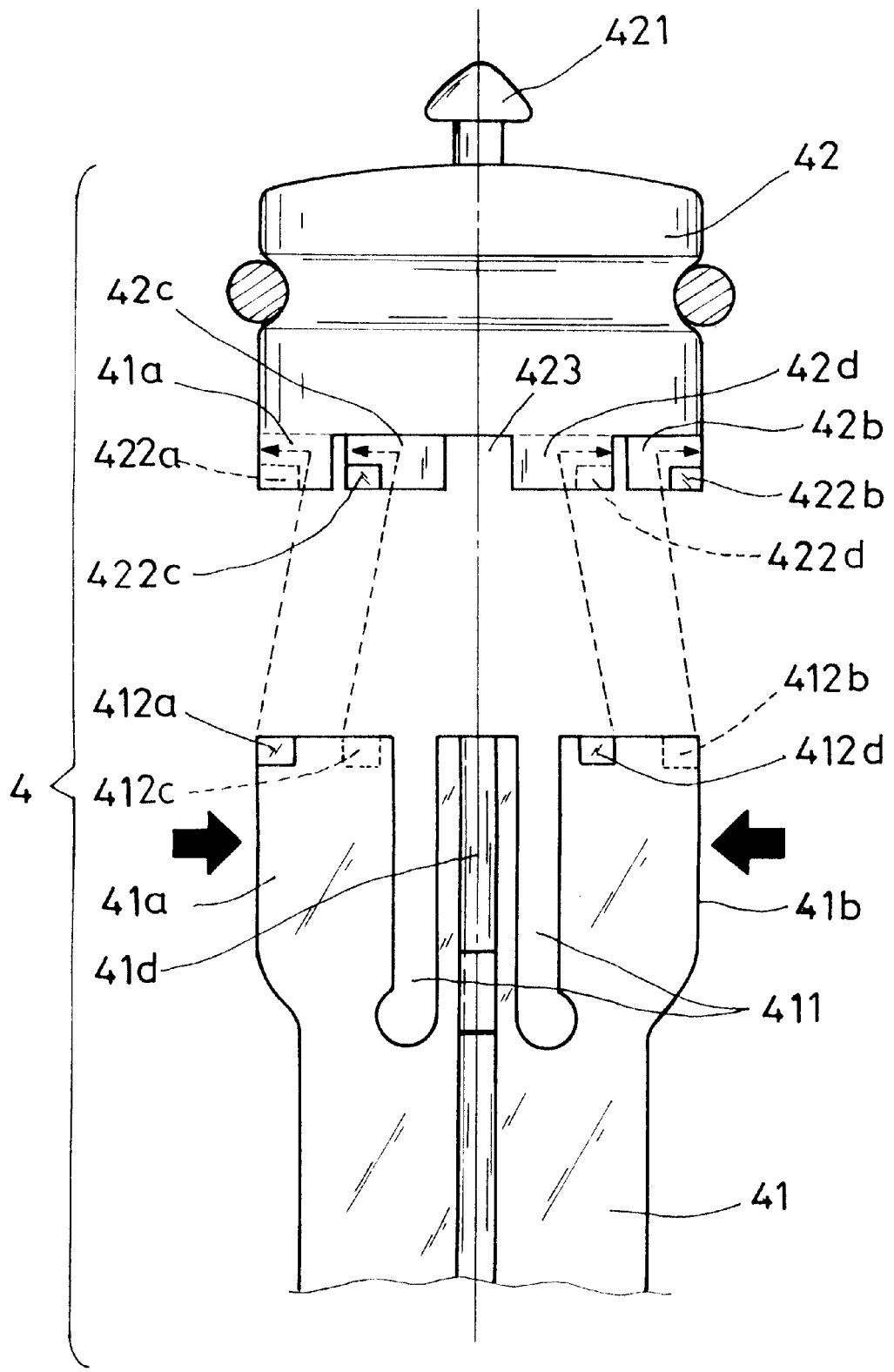
FIG. 7 is a schematic side view of the plunger and stopper unit of the safety hypodermic syringe according to the present invention, showing the front wings compressed and inserted into the crossed receiving space in the bottom side of the stopper.
Figure 8:
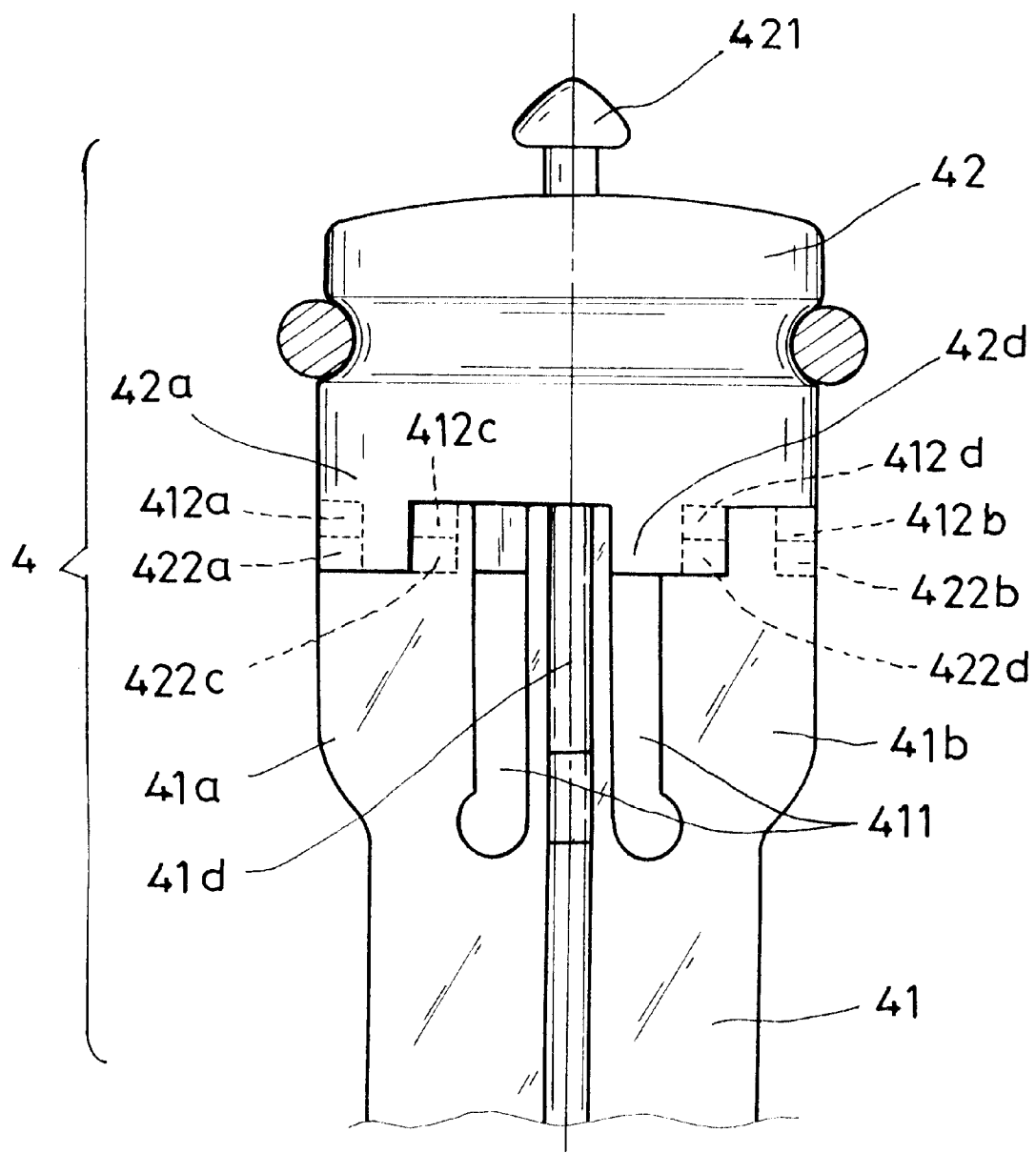
FIG. 8 is a schematic side view of the plunger and stopper unit of the safety hypodermic syringe according to the present invention, showing the plunger fastened to the stopper.

FIG. 7 is a plain view of the plunger 4. The left and right front wings 41a and 41b are radially compressed inwards to close the respective crevices 411 for enabling the four front wings 41a, 41b, 41c, and 41d of the plunger 41 to be inserted into the crossed receiving space 423 in the bottom side of the stopper 42. After insertion of the four front wings 41a, 41b, 41c, and 41d into the crossed receiving space 423 and release of radial compressive force from the left and right front wings 41a and 41b, the left and right front wings 41a and 41b are returned to their former shape to force the respective retaining blocks 412a and 412c, 412b, and 412d into engagement with the corresponding protruded engagement portions 422a, 422b, 422c, or 422d of the locating blocks 42a, 42b, 42c, and 42d, and therefore the plunger 41 is secured to the stopper 42 (see FIG. 8).

Figure 9:
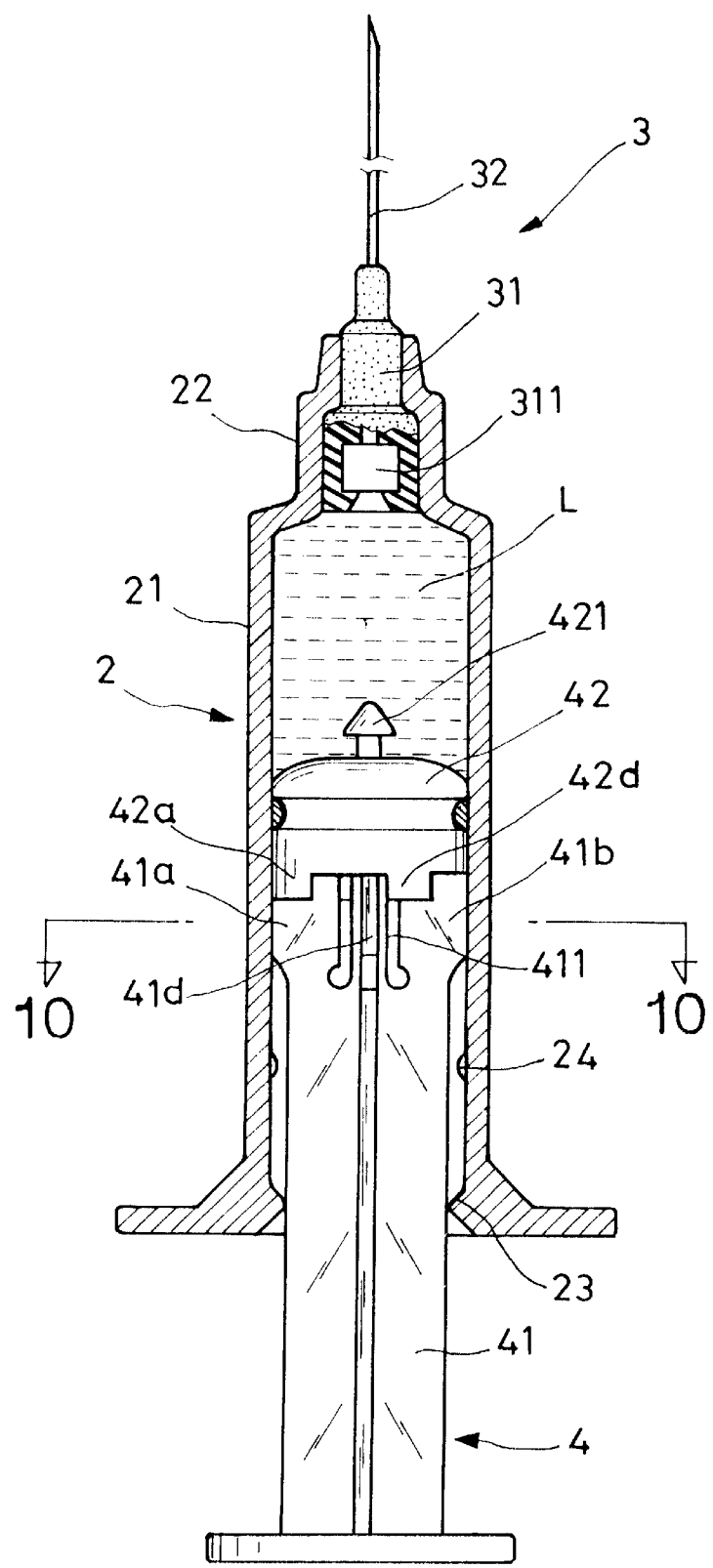
FIG. 9 is a schematic side view of the present invention, showing a status of use of the safety hypodermic syringe.

FIG. 9 is a schematic sectional view, showing a status of use of the safety hypodermic syringe. As illustrated, the plunger and stopper unit 4 is pushed forwards to force liquid medicine L out of the needle cannula 32. When the plunger and stopper unit 4 moved to the upper limit position, the arrowhead-like hook 421 of the stopper 42 is forced into engagement with the bottom retaining hole 311 of the needle hub 31 for enabling the needle assembly 3 to be received inside the barrel 2 upon a back stroke of the plunger and stopper unit 4.

Figure 10:
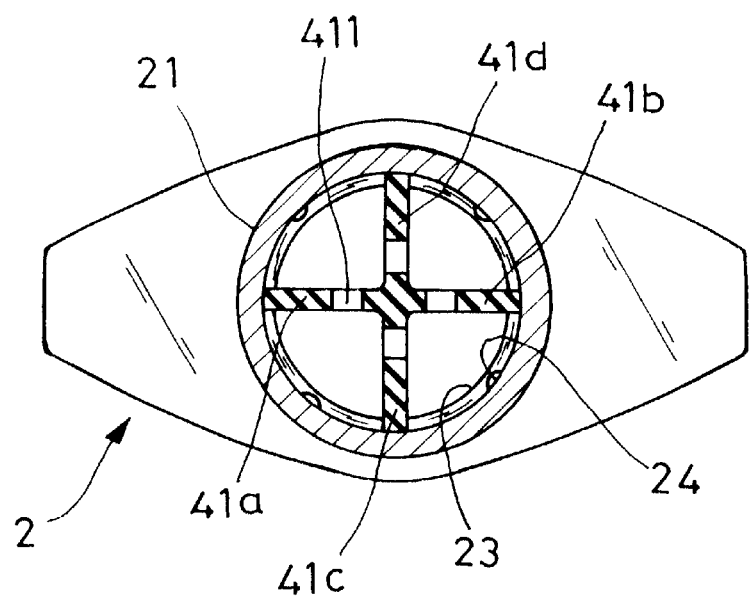
FIG. 10 is a sectional view taken along line 10—10 of FIG. 9.
Figure 11:
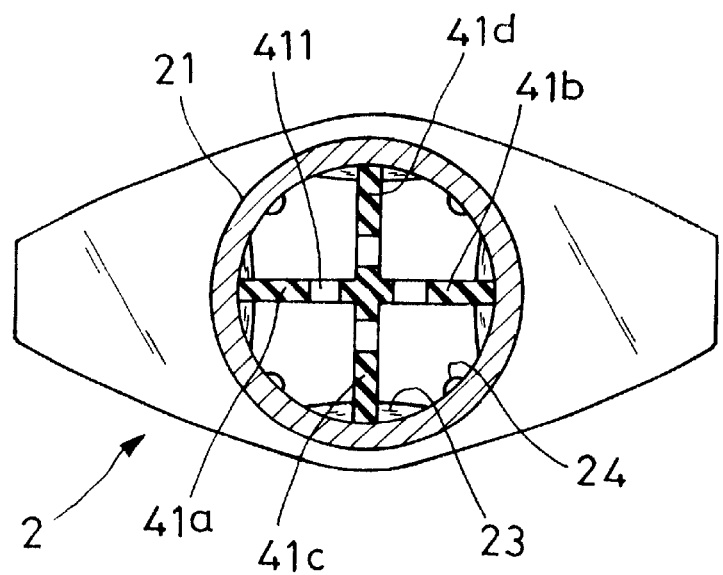
FIG. 11 is similar to FIG. 10 but showing an alternate form of the stop device.

Referring to FIGS. 10 and 11 and FIG. 9 again, the body 21 of the barrel 2 has a stop device 23 at the rear side adapted to stop the stopper 42 from falling out of the barrel 2 upon a backstroke of the plunger and stopper unit 4. The stop device 23 may be variously embodied. For example, the stop device 23 can be an inside annular flange protruded from the inside wall of the body 21 of the barrel 2 as shown in FIG. 10, or comprised of a plurality of blocks protruded from the inside wall of the body 21 of the barrel 2 as shown in FIG. 11. The body 21 of the barrel 2 can be made having small raised portions 24 on the inside above the stop device 23. The small raised portions 24 are not requisite. The effect of the small raised portions 24 will be explained latter.

Figure 12:
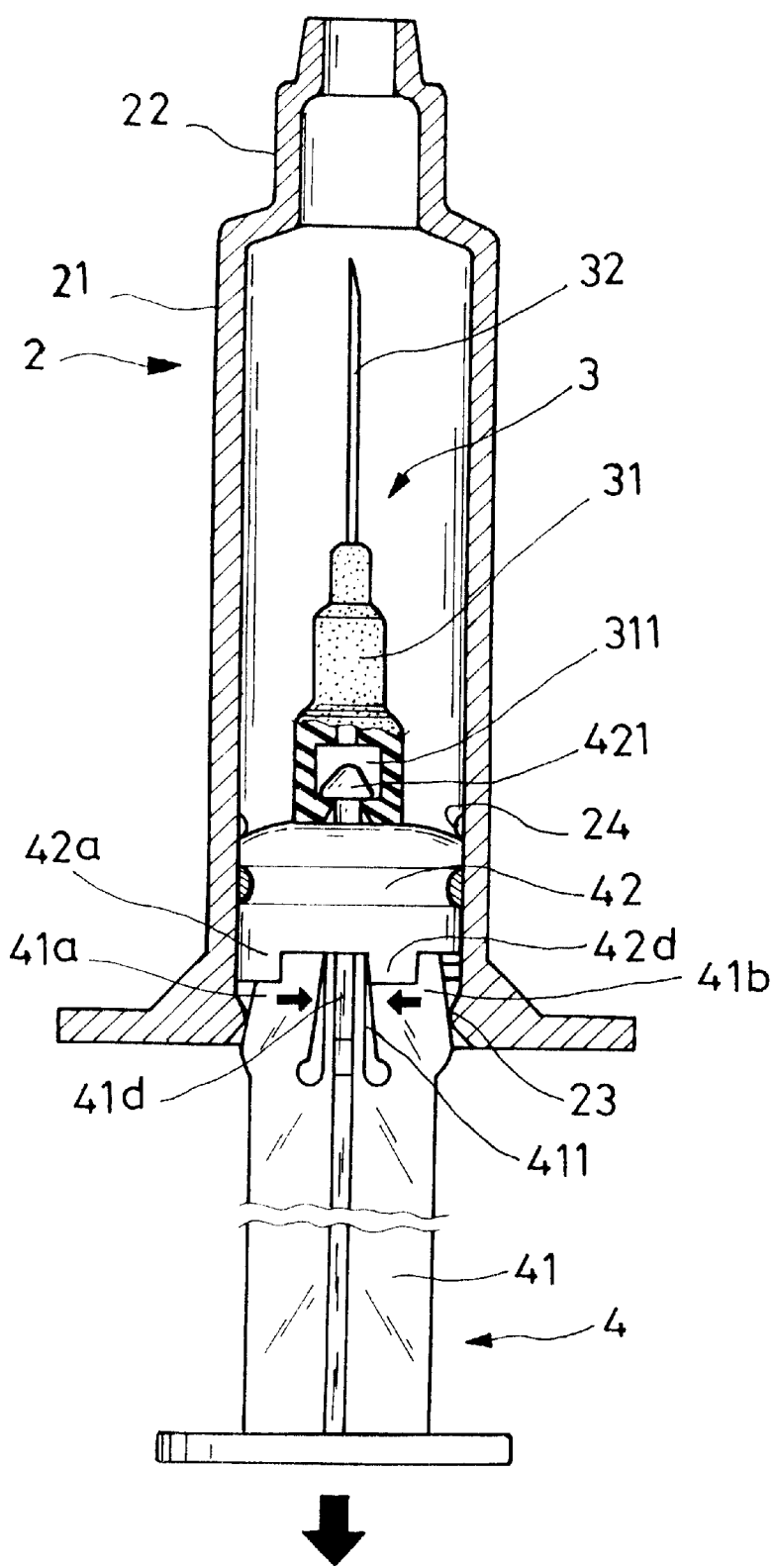
FIG. 12 is a schematic side view of the present invention, showing the return stroke of the plunger and stopper unit.
Figure 13:
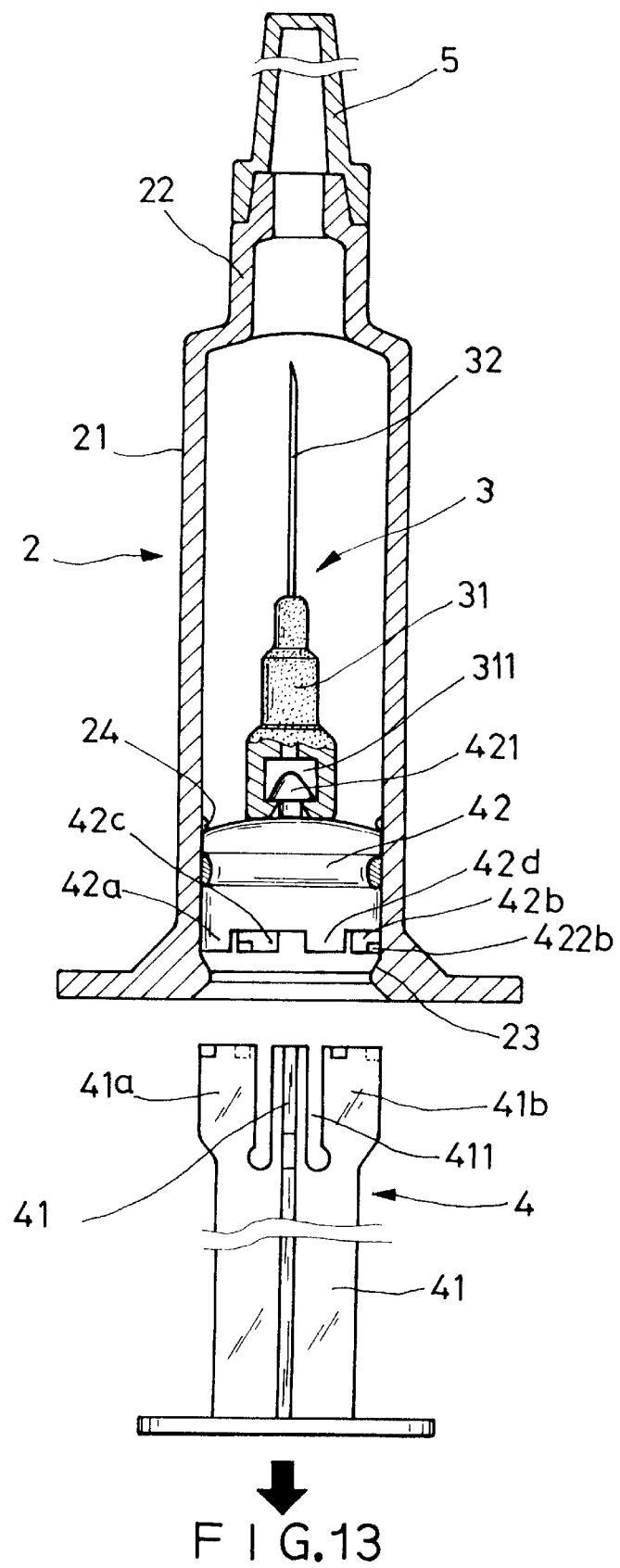
FIG. 13 is similar to FIG. 12 but showing the plunger disconnected from the stopper.

FIG. 12 illustrates a status of use of the safety hypodermic syringe after return stroke of the plunger and stopper unit 4. When the plunger 41 pulled backwards to the rear side of the barrel 2, the front wings 41a, 41b, 41c, and 41d are radially inwardly forced by the stop device 23 to close the respective crevices 411, thereby causing the respective retaining blocks 412a and 412c, 412b, and 412d to be disengaged from the corresponding protruded engagement portions 422a, 422b, 422c, and 422d of the locating blocks 42a, 42b, 42c, and 42d, and therefore the plunger 41 is disconnected from the stopper 42, leaving the stopper 42 and the needle assembly 3 inside the barrel 2 (see FIG. 13).

Referring to FIG. 13 again, after removal of the plunger 41 from the stopper 42, the cap 5 is covered on the front socket 22 to close the barrel 2. At this time, the stopper 42 is retained inside the body 21 of the barrel 2 between the small raised portions 24 and the stop device 23, holding the needle assembly 3 inside the barrel 2. Because the stopper 42 is an elastic member, it can be deformed to pass over the raised portions 24 when pulled backwards by the plunger 41. After removal of the plunger 41 from the stopper 42, the stopper 42 is firmly stopped between the small raised portions 24 and the stop device 23.

A prototype of safety hypodermic syringe has been constructed within the features of FIGS. 4~13. The safety hypodermic syringe functions smoothly to provide all the features discussed earlier.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A safety hypodermic syringe comprising:

a barrel, said barrel comprising a body and a socket at a front side of said body;

a needle assembly, said needle assembly comprising a needle hub mounted in said front socket of said barrel, said needle hub having a bottom retaining hole, and a needle cannula forwardly extended from said needle hub outside said barrel; and a plunger and stopper unit, said plunger and stopper unit comprising a stopper fitted into said body of said barrel, and an elongated plunger adapted to reciprocate said stopper in said body of said barrel, said stopper having an arrowhead-like front hook engageable into a bottom retaining hole of said needle hub for enabling said needle assembly to be pulled backwards with said plunger and stopper unit and received inside said body of said barrel;

wherein said barrel has a stop device in a rear side of said body and adapted to stop said stopper from falling out of said body; said plunger comprises a plurality of equiangularly spaced and radially extended springy front wings, said front wings each having a crevice longitudinally extended to a front side thereof, said front wings including two opposite front wings, said opposite front wings each having a plurality of retaining blocks; said stopper has a plurality of locating blocks protruded from a bottom sidewall thereof and defining a receiving space adapted to receive the front wings of said plunger, said locating blocks each having a protruded engagement portion adapted to engage the retaining blocks of the opposite front wings of said plunger and to secure said plunger to said stopper.

2. The safety hypodermic syringe as claimed in claim 1, wherein said body of said barrel has a plurality of small raised portions protruding from an inside wall thereof and spaced above said stop device.

3. The safety hypodermic syringe as claimed in claim 1, wherein said stop device of said barrel is an inside annular flange formed integral with an inside wall of said body.

4. The safety hypodermic syringe as claimed in claim 1, wherein said stop device of said barrel is comprised of a plurality of blocks protruded from an inside wall of said body.

5. The safety hypodermic syringe as claimed in claim 1, wherein said opposite front wings each have two retaining blocks reversely protruded at two sides.

6. The safety hypodermic syringe as claimed in claim 1, wherein the number of said locating blocks of said stopper is 4, and the receiving space defined by the locating blocks of said stopper is a crossed receiving space.

7. The safety hypodermis syringe as claimed in claim 1, further comprising a cap for closing on the front socket of said barrel to protect said needle assembly.

* * * * *